United States Patent
Waki

(10) Patent No.: US 7,267,796 B2
(45) Date of Patent: Sep. 11, 2007

(54) PREPARATIVE LIQUID CHROMATOGRAPH USING PLURAL DETECTORS

(75) Inventor: Hiroaki Waki, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 614 days.

(21) Appl. No.: 10/617,021

(22) Filed: Jul. 11, 2003

(65) Prior Publication Data
US 2004/0018118 A1   Jan. 29, 2004

(30) Foreign Application Priority Data
Jul. 12, 2002   (JP)   ............................. 2002-204161

(51) Int. Cl.
   *G01N 30/86* (2006.01)
(52) U.S. Cl. .................. 422/70; 422/89; 210/198.2; 210/656; 95/82; 96/101; 96/102; 73/23.36; 73/23.37; 73/61.57; 73/61.58; 702/22; 702/23; 702/24; 702/25; 436/161; 436/164; 436/173
(58) Field of Classification Search ................ 436/161, 436/164, 173; 422/70, 89; 210/198.2, 656; 95/82; 96/101, 102; 73/23.36, 23.37, 61.57, 73/61.58; 700/12; 702/22–25
See application file for complete search history.

(56) References Cited

U.S. PATENT DOCUMENTS

| | | | | |
|---|---|---|---|---|
| 5,670,054 | A | * | 9/1997 | Kibbey et al. ............... 210/656 |
| 5,938,932 | A | * | 8/1999 | Connelly et al. ............ 210/659 |
| 6,413,431 | B1 | * | 7/2002 | Abedi ........................ 210/656 |
| 2002/0074490 | A1 | | 6/2002 | Umemura ................... 250/288 |
| 2002/0121468 | A1 | * | 9/2002 | Fischer et al. ........... 210/198.2 |

FOREIGN PATENT DOCUMENTS

| | | |
|---|---|---|
| EP | 1 162 456 | 12/2001 |
| JP | 53-4594 | 1/1978 |

(Continued)

OTHER PUBLICATIONS

Kiplinger et al., Rapid Communications in Mass Spectrometry 12, 658-664 (1998).*

(Continued)

*Primary Examiner*—Jan M. Ludlow
(74) *Attorney, Agent, or Firm*—Westerman, Hattori, Daniels & Adrian, LLP.

(57) ABSTRACT

The preparative liquid chromatograph uses a plurality of detectors including a mass spectrometer, and a chromatogram generator is provided for generating a plurality of chromatograms each corresponding to each of the plurality of detectors. The plurality of chromatograms are converted into a respective binary signal by comparing the chromatogram with a predetermined threshold, and a logical operator performs a binary operation on the plurality of respective binary signals, whereby a resultant binary signal is generated. A separation controller controls the fraction collector of the preparative liquid chromatograph based on the resultant binary signal to separate components from a sample. When "AND" is used as the binary operation, the resultant binary signal is "1" only when all the respective binary signals are "1". This assures a high precision, high purity separation where an impurity mingling is minimized. When "OR" is adopted as the binary operation, the resultant binary signal is "1" when a component is detected by any of the plurality of detectors. This assures separation of as many components as possible appearing in the chromatograms generated by the detectors.

6 Claims, 3 Drawing Sheets

FOREIGN PATENT DOCUMENTS

| | | |
|---|---|---|
| JP | 64-54351 | 3/1989 |
| JP | 3-29850 | 2/1991 |
| JP | 4-138358 | 5/1992 |
| JP | 4-326058 | 11/1992 |
| JP | 10-19868 | 1/1998 |
| JP | 10-197506 | 7/1998 |
| WO | WO 97/38303 | 10/1997 |
| WO | WO 99/25452 | 5/1999 |

OTHER PUBLICATIONS

Rosentreter et al, Journal of Combinatorial Chemistry, vol. 6, No. 2, 159-164 (Mar./Apr. 2004; published on Web Jan. 17, 2004).*

Stevens et al. "A Multipurpose Preparative System for the Detection and Collection of Active and Non-Active UV/Vis Compounds" www.gilson.com.*

Mazza, "Purification Solutions for Today's Scientists" PittCon 2005, Orlando, FL, Feb. 28, 2005.*

Waters, Autopurification Systems Fractionlynx MS, Fractionlynx UV brochure, May 2001.*

Zeng, L. et al., "Automated analytical/preparative high-performance liquid chromatography-mass spectrometry system for the rapid characterization and purification of compound libraries", Journal of Chromatography A, Elsevier Science, NL, vol. 794, 1998, pp. 3-13.

* cited by examiner

PREPARATIVE LIQUID CHROMATOGRAPH USING PLURAL DETECTORS

The present invention relates to a preparative liquid chromatograph ("preparative LC") which is used to separate a component or components from a sample employing a chromatograph such as the high performance liquid chromatograph (HPLC).

BACKGROUND OF THE INVENTION

A typical preparative LC using the HPLC is shown in FIG. 5. The eluent (or the "moving phase") in the eluent tank 1 is drawn by a pump 2 and is sent at a constant flow rate to the column 4 via the sample injector 3. The sample injected at the sample injector 3 is carried by the eluent to the column 4, where the components of the sample are separated in the course of time. The separated components flow out of the other end of the column 4 one after another. The detector 5 ("UV detector" in FIG. 5) detects the components flowing out of the column 4, and sends corresponding signals to the signal processor 6. All of or a part of the eluate passing through the detector 5 is introduced into the fraction collector 8. The signal processor 6 generates a chromatogram based on the signals sent from the detector 5, and the separation controller 7 sends signals to the fraction collector 8 based on the peaks appearing in the chromatogram. According to the signals from the separation controller 7, the fraction collector 8 operates the control valves to the respective vials to batch off (or separate) the components.

For the detector of many kinds of preparative LCs, the ultraviolet-visible light spectrophotometer ("UV detector") using a photodiode array detector has been widely used. Recently, though, a mass spectrometer ("MS") has begun to be used as the detector. When an MS is used, the components contained in the sample are detected with their mass to charge ratios, which enables the separation of components even if they have the same or close retention time of the liquid chromatograph. Thus, by using the liquid chromatograph mass spectrometer (LCMS) including an MS as the detector, it is possible to batch off components more accurately than before.

FIG. 6 shows a schematic structure of a preparative LC using an MS as the detector. Same or similar elements to those in FIG. 5 are labeled the same, and the description above is applied the same as above. Since, in the MS 9, the components of the sample to be detected are ionized, the eluent is consumed there, which means that it is impossible to separate the eluate that has passed through the MS 9. Instead of this being a drawback, it has the advantage that the amount of eluate necessary for the detector 9 is very small. Thus, the current LCMS adopts the following structure. A splitter 11 is provided between the column 4 and the MS 9, and only a very small part of the eluate flowing out of the column 4 of the liquid chromatograph is given to the MS 9, while most of the rest of the eluate is sent to the fraction collector 8.

In many HPLCs, a so-called multiple detection system is adopted in which an UV detector or an evaporation light scattering detector (ELSD) is used as well as the MS detector. Such a system is adopted because a single detector cannot cover all the object components. Respective detectors used in a multiple detection system detect an appropriate component or components, and they complementarily detect all the components contained in a sample. This improves the detection accuracy and prevents any detection miss. Such a multiple detection system is presumed to be also useful for the preparative LC using the fraction collector. But in conventional preparative LCs using the multiple detection system, the separation of components of a sample is performed based on the detection signals of the plural detectors, where the detection signals are chosen arbitrarily. Thus the advantage of the multiple detection system as described above is not fully realized.

SUMMARY OF THE INVENTION

The present invention addresses the problem. An object of the present invention is, therefore, to provide a preparative LC using a multiple detection system which can batch off components from a sample at high accuracy.

According to the present invention, a preparative liquid chromatograph comprises:
a plurality of detectors including a mass spectrometer;
a chromatogram generator for generating a plurality of chromatograms each corresponding to each of the plurality of detectors;
a binary converter for converting each of the plurality of chromatograms into a respective binary signal by comparing the chromatogram with a predetermined threshold;
a logical operator for performing a binary operation on the plurality of respective binary signals and for generating a resultant binary signal; and
a separation controller for controlling a fraction collector of the preparative liquid chromatograph based on the resultant binary signal to separate components from a sample.

In the preparative LC according to the present invention, the ultraviolet-visible light spectrophotometer (UV detector), an evaporation light scattering detector (ELSD), etc. can be used as the detector, as well as the mass spectrometer. The eluate flowing out of the column is successively sent to the detectors, or is split to give a respective part to every detector. In every detector, the components of the sample included in the eluate are detected according to an appropriate detecting method. Every detector detects the components in the course of time, and generates a detection signal, which is sent to the chromatogram generator. The chromatogram generator generates a chromatogram based on the signal from every detector, so that plural chromatograms corresponding to the number of detectors are generated. The binary converter converts a chromatogram to a respective binary signal by comparing every value of a chromatogram with a predetermined threshold. The value of the threshold can be determined by the operator.

The respective binary signal is generated for every chromatogram. A respective binary signal is composed of a series of 0s and 1s, which means that the pertinent components are present or not. The logical operator performs a predetermined binary operation, for example "AND", "OR", "EXCLUSIVE OR" and their combination, on the respective binary signals, and generates a resultant binary signal. The separation controller determines the timing of separating respective components based on the resultant binary signal, and controls the fraction collector to batch off the components.

The operation is described in detail. When "AND" is used as the binary operation, the resultant binary signal is "1" only when all the respective binary signals are "1", or only when a component is detected by all detectors. This assures high precision and high purity separation, where an impurity mingling is minimized. When "OR" is adopted as the binary operation, the resultant binary signal is "1" when a component is detected by any of the plurality of detectors. This assures separation of as many components as possible appearing in the chromatograms generated by the detectors.

Thus the preparative LC of the present invention enables a higher precision separation taking full advantage of plural detectors if an appropriate logical operator is used. On the other hand, when the amount of the object component is not enough, the object component can be surely separated without loss by using another appropriate logical operator, although the inclusion of some other component may be anticipated. Other modes of separation are also possible by employing appropriate logical operators.

When a plurality of detectors are used, the time for the eluate to arrive at respective detectors varies, and the time for the respective detectors to generate the detection signals from the arrival of the eluate varies. Those time differences cause the peaks of the same component in the chromatograms shift in the time axis.

In order to cancel the shift time in the chromatograms of the detectors, another type of preparative LC according to the present invention includes, in addition to the element described above, a shift time determiner for determining a shift time between a plurality of chromatograms; and a shift time canceller for canceling the shift time between the plurality of chromatograms.

The shift time canceller may cancel the shift time on the chromatograms, i.e., before a chromatogram is converted to a binary signal, or after that.

This type of preparative LC enables a still higher precision separation of components. If such a shift time is intended to be canceled by modifying the piping configuration of the eluate, the structure could be complicated and the cost would increase. In the preparative LC of the present invention, the shift time is canceled by electrical measures, so that the canceling is precise and the cost is reduced.

DETAILED DESCRIPTION OF A PREFERRED EMBODIMENT

Figure 1:
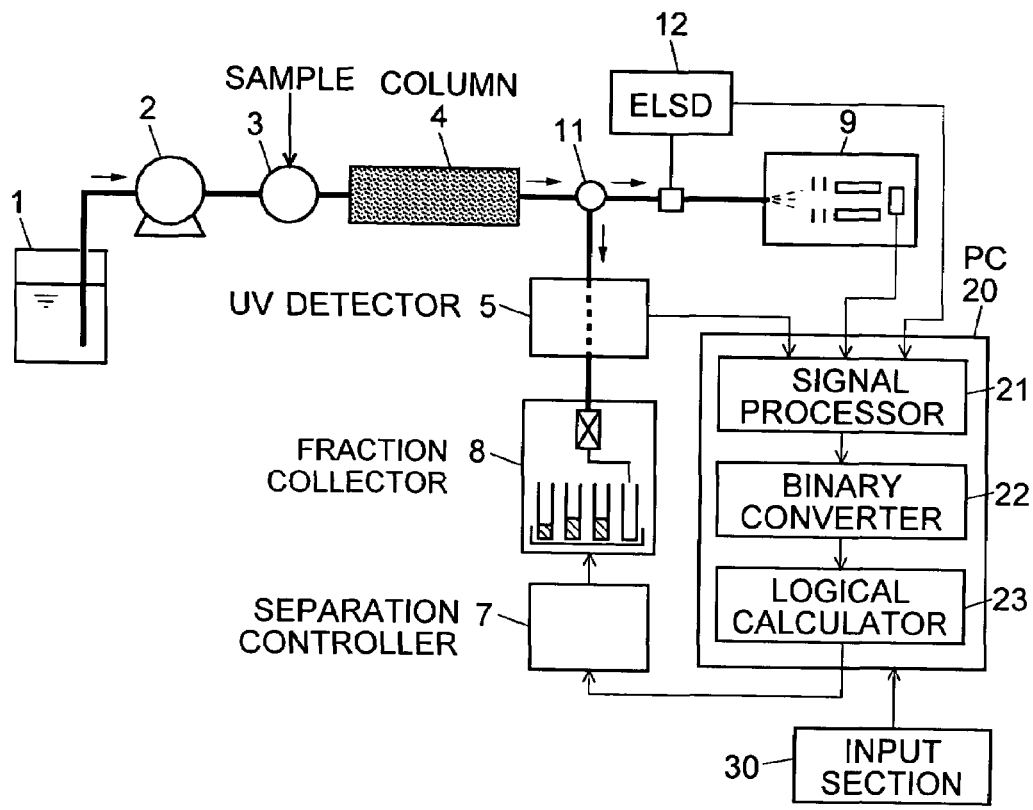
FIG. 1 is a schematic diagram of a preparative LC embodying the present invention.
Figure 5:
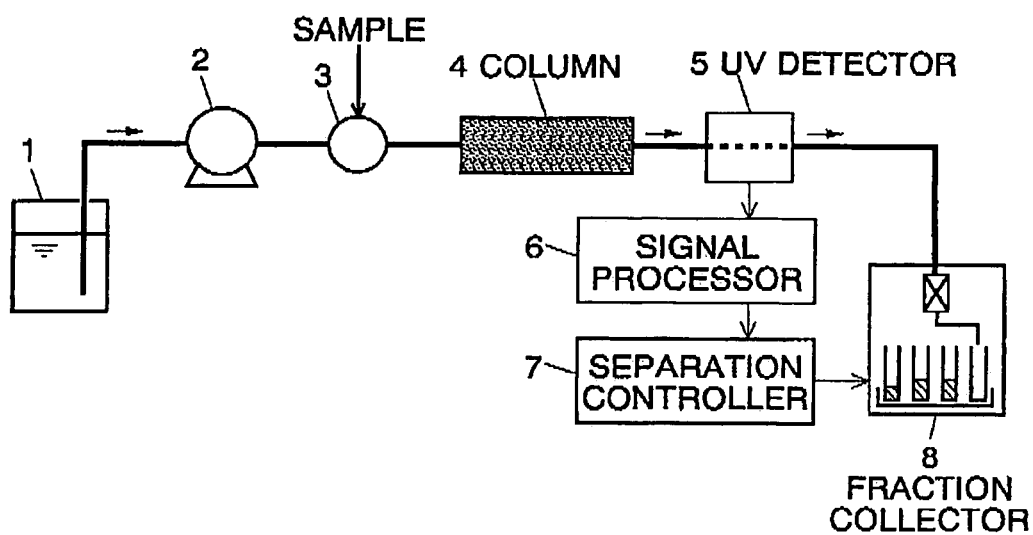
FIG. 5 is a schematic diagram of a conventional preparative LC using a UV detector.
Figure 6:
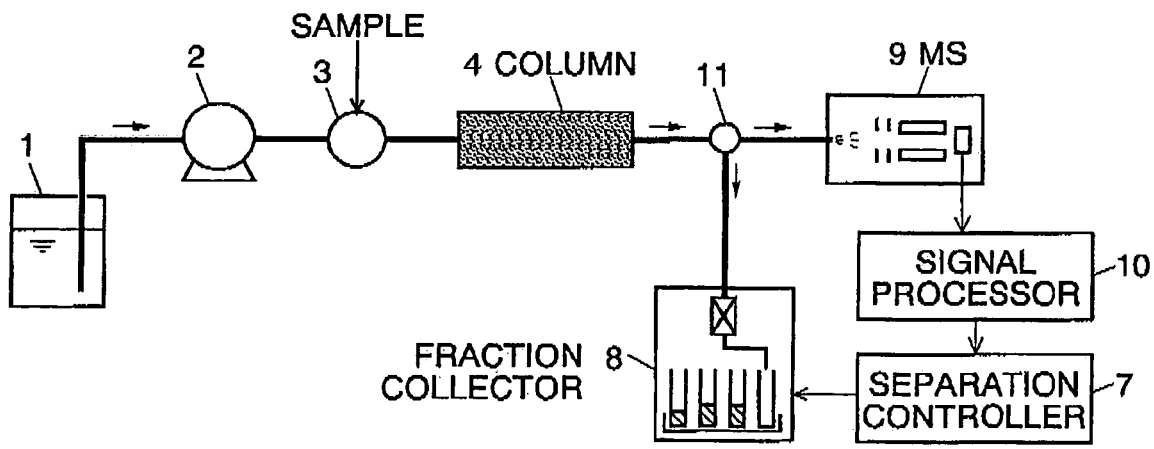
FIG. 6 is a schematic diagram of a conventional preparative LC using an MS detector.

A preparative LC embodying the present invention is shown in FIG. 1, where elements the same or similar to those in FIGS. 5 and 6 are numbered the same and the same description as above applies.

At the exit of the column 4 of the preparative LC, a splitter 11 is provided where the sample liquid flowing out of the column 4 is divided into two flows at a predetermined share ratio. One flow is led to the MS 9 and the ELSD 12, and the other flow is led to the fraction collector 8 via the UV detector 5. The detection signals from the three detectors, i.e., MS 9, ELSD 12 and UV detector 5, are sent to the signal processor 21, where chromatograms are constructed using respective signals. The signal processor 21 may be realized by a personal computer (PC) with an appropriate signal processing program. The chromatograms are given to the binary converter 22, where the chromatograms are compared with a preset threshold value and are converted to a series of binary signals of "0"s and "1"s. The logical calculator 23 sequentially performs logical operations on at least two of the three binary signals. The results are sent to the separation controller 7. An input section 30 is connected to the personal computer 20, where the operator can give commands of analyzing conditions to the personal computer 20. The analyzing conditions include the threshold value used in the binary converter 22 and the logical operation formulae used in the logical calculator 23.

As is well known, mass spectra are successively obtained in the MS 9. Using the mass spectra, a total chromatogram can be obtained as well as mass chromatograms. A total chromatogram is a chromatogram composed of an accumulation of all the detected ions, and a mass chromatogram is a chromatogram composed of a specific mass to charge ratio. Either of the total chromatogram or the mass chromatogram can be converted to the binary signal in the binary converter 22, but normally the total chromatogram is used. The mass chromatogram is used for other special purposes.

In the UV detector 5, absorption spectra are successively obtained. By detecting the maximum value of the absorption spectra, and placing the maximum values in a row according to the order of time, a chromatogram is obtained. It is also possible to construct a chromatogram by collecting the absorptions at a specific wavelength.

Figure 2:
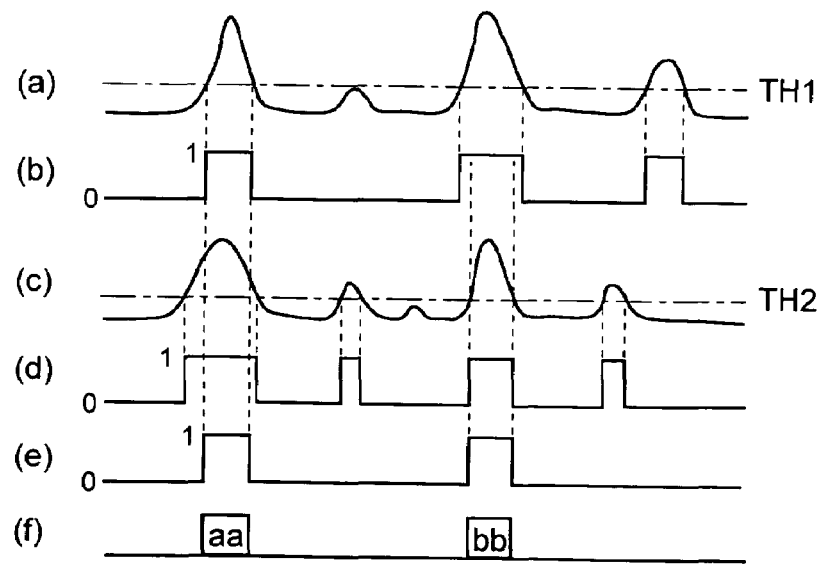
FIG. 2 is timing charts of chromatograms and binary signals when an "AND" operator is used.
Figure 3:
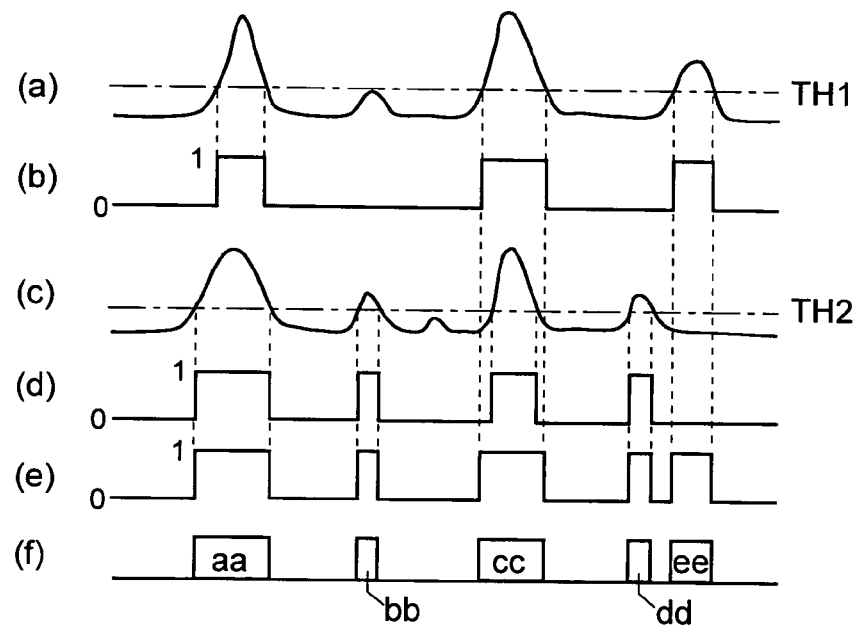
FIG. 3 is timing charts of chromatograms and binary signals when an "OR" operator is used.

The preparative LC works as follows. First, the object sample is injected before the column 4 and a preparatory analysis is performed, whereby the separation timings are determined. Then the object sample is again injected before the column 4 and the proper separation is performed. FIGS. 2 and 3 show the chromatograms obtained by the detectors and the separation timings determined from the chromatograms. The graphs of (a) through (d) are the same in FIG. 2 and in FIG. 3.

Since the preparative LC of the present embodiment uses three detectors, three chromatograms are constructed in the signal processor 21, where each chromatogram is made based on each detector. Because the detecting methods are different in the three detectors, the shapes and heights of the same peak are different in the three chromatograms. It should be noted here that the time difference of the same peak between different detectors are disregarded. It is supposed here that a detector produced the chromatogram (a) and another detector produced the chromatogram (b) in the preparatory analysis.

The two chromatograms as a whole have a similar shape, but corresponding peaks of the two chromatograms have different heights and widths. Looking at the graph of each chromatogram, the operator determines an appropriate threshold value TH1 or TH2, as shown in (a) and (c) of FIG. 2. The binary converter 22 compares every piece of data of a chromatogram with the threshold value TH1 or TH2, and produces a binary signal "0" or "1" according to the comparison result. Thus a chromatogram is converted to a series of binary data as shown (b) or (d) of FIG. 2. In the binary graph of (b) or (d), the "0" period implies no peak, and "1" period implies a peak.

When the operator intends to batch off components when the corresponding peak appears in both chromatograms, he/she sets the logical operation "AND" in the logical calculator 23 through the input section 30. In this case, the "AND" operation is performed on the binary signals (b) and (d) of the two detectors, and the resultant binary signal as shown in (e) of FIG. 2 is obtained in the logical calculator 23. In the "1" period of the graph of (e) of FIG. 2, the corresponding peak appears in both chromatograms. The resultant signal is sent from the logical calculator 23 to the separation controller 7. After the preparatory analysis is thus finished, a proper separation operation is started and the separation controller 7 controls the fraction collector 8 according to the binary signal, where the components aa and bb are batched off from the sample into separate vials as shown in (f) of FIG. 2. This method assures separation of components at high precision.

When the operator intends to batch off components whose peaks appear in any of the chromatograms, he/she sets the logical operation "OR" in the logical calculator 23. In that case, the "OR" operation is performed on the binary signals (b) and (d) of the two detectors, and the resultant binary signal as shown in (e) of FIG. 3 is obtained in the logical calculator 23. In the "1" period of the graph of (e) of FIG. 3, the corresponding peak appears in either chromatogram. The resultant signal is sent from the logical calculator 23 to the separation controller 7. After the preparatory analysis is thus finished, a proper separation operation is started and the separation controller 7 controls the fraction collector 8 according to the binary signal, where the components aa, bb, cc, dd and ee are batched off from the sample into separate vials as shown in (f) of FIG. 3. This method assures separation of as many components as possible.

In the above example, only two chromatograms, or detectors, are used for simplicity of explanation. It is of course possible to use three or more chromatograms, or detectors, and further complicated logical operations, which provides the operator with various ways of separation according to his/her intention.

In the above example, the time shifts of the chromatograms of respective detectors are disregarded. But actually there are time shifts in the three chromatograms due to the time difference of eluate arriving at the detectors 5, 6 and 12, which depends on the diameter and length of the pipe, flow rate and flowing amount of the eluate. It is possible, though, to eliminate the time difference by adequately designing the pipe and the eluate flow, but it complicates the construction of the preparative LC and raises the cost. Even if the arriving times of the eluate to the detectors are equalized, every detector has its own detection delay, whereby the chromatograms also diverge. The construction of a preparative LC shown in FIG. 4, which is the second embodiment of the present invention, addresses the problem.

Figure 4:
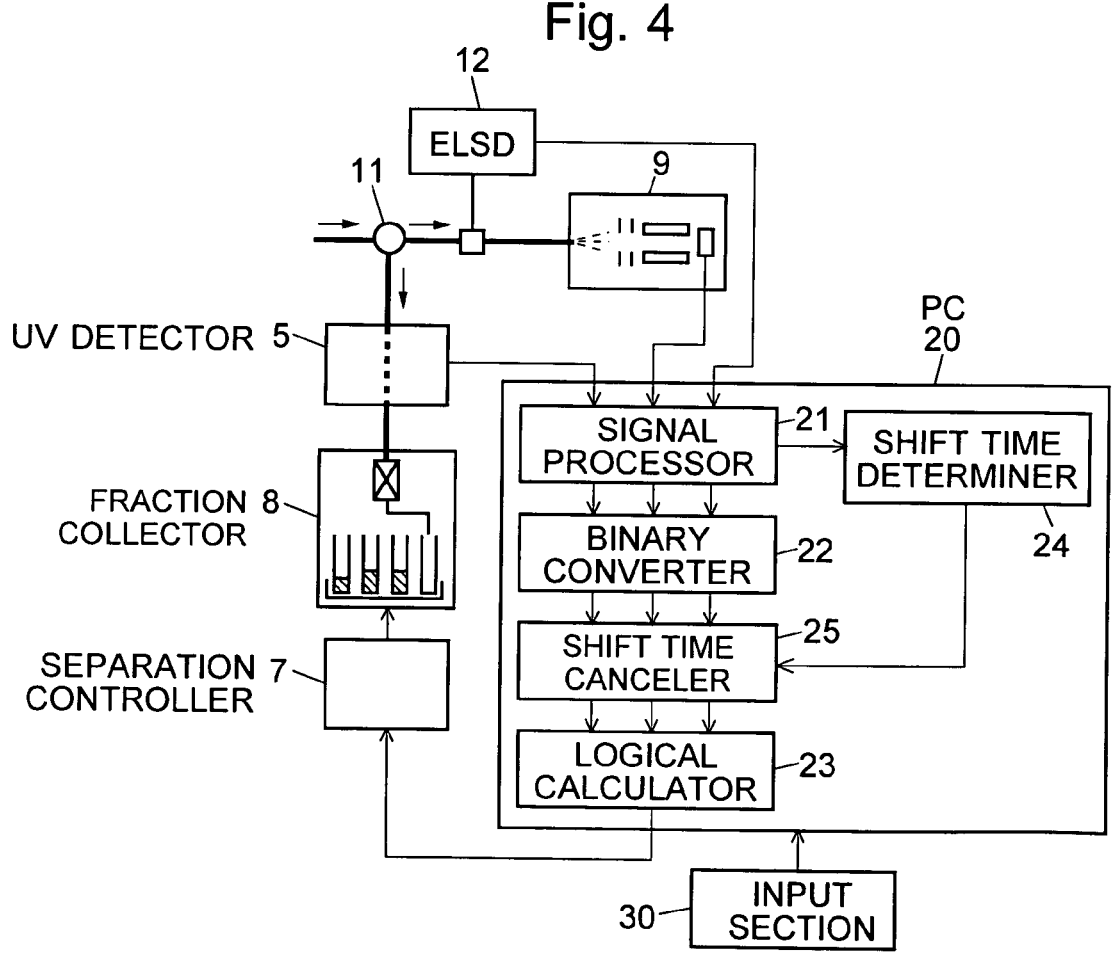
FIG. 4 is a schematic diagram of another preparative LC embodying the present invention.

The portion of the preparative LC before the splitter is omitted in FIG. 4 because it is the same as that of FIG. 1. In the preparative LC of the second embodiment, the shift time determiner 24 and the shift time canceller 25 are added. The shift time determiner 24 calculates the shift time between chromatograms based on the signals from the signal processor 21. The shift time canceller 25 is placed after the binary converter 22, and add (or subtract) an appropriate shift time, based on the signal from the shift time determiner 24, to every binary signal sent from the binary converter 22.

The operation of the preparative LC of the second embodiment is as follows. In the preparatory analysis as described above, the shift time determiner 24 detects the same peak of a certain component (preferably, a known component of a standard sample) in the chromatograms, and calculates the shift times between the chromatograms. The values of the shift times are stored in the memory. When the proper separation operation is performed, data of the shift times are given to the shift time canceller 25, which gives the delay of the shift time to the binary signal of a chronologically preceding chromatogram. Owing to the introduction of the delays, the binary signals are synchronized to the same timing as to the detection of the components, and the logical operations on the binary signals can be performed exactly. The time shift can be made either on the binary signals or on the chromatograms. But it is normally easier to introduce the time shift in the binary signals.

The above description of embodiments are just examples, and it is obvious for a person skilled in the art to modify the embodiments within the scope of the present invention. For example, a personal computer 20 with an appropriate program is used to process the signal and perform the logical operations in the above embodiments. It is clear that it can be replaced by a proper hardware including components for performing parallel functions. In the above embodiments, commonly found detectors, i.e., a UV detector 5, MS 9 and ELSD 12, are used. It is of course possible to use other kinds of detectors. It is also possible to use a unified detector which contains plural detectors and sends out output signals from respective detectors in parallel. Such a detector is described in the Publication No. 2002-372516 of Unexamined Patent Application.

What is claimed is:

1. A preparative liquid chromatograph comprising:
a plurality of detectors including a mass spectrometer;
a chromatogram generator for generating a plurality of chromatograms each corresponding to each of the plurality of detectors;
a binary converter for converting each of the plurality of chromatograms into a respective binary signal by comparing the chromatogram with a predetermined threshold;
a logical operator for performing a binary operation on the plurality of respective binary signals and for generating a resultant binary signal; and
a separation controller for controlling a fraction collector of the preparative liquid chromatograph based on the resultant binary signal to separate components from a sample,
wherein the binary operation performed in the logical operator is AND of all the respective binary signals.

2. The preparative liquid chromatograph according to claim 1, wherein the plurality of detectors include an ultraviolet-visible light spectrophotometer (UV detector) and an evaporation light scattering detector (ELSD) as well as the mass spectrometer.

3. The preparative liquid chromatograph according to claim 1, wherein the preparative liquid chromatograph further comprises:
a shift time determiner for determining a shift time between a plurality of chromatograms; and
a shift time canceller for canceling the shift time between the plurality of chromatograms.

4. The preparative liquid chromatograph according to claim 1, wherein the preparative liquid chromatograph further comprises:
a shift time determiner for determining a shift time between a plurality of chromatograms; and
a shift time canceller for canceling the shift time between the plurality of respective binary signals corresponding to the plurality of chromatograms.

5. The preparative liquid chromatograph according to claim 3, wherein the shift time determiner determines the shift time between the plurality of chromatograms by measuring a shift time between peaks of the same component contained in a standard sample.

6. The preparative liquid chromatograph according to claim 4, wherein the shift time determiner determines the shift time between the plurality of chromatograms by measuring a shift time between peaks of the same component contained in a standard sample.

* * * * *